(12) United States Patent
Landvik et al.

(10) Patent No.: US 9,404,093 B2
(45) Date of Patent: Aug. 2, 2016

(54) POLYPEPTIDES HAVING PEROXYGENASE ACTIVITY AND POLYNUCLEOTIDES ENCODING SAME

(71) Applicant: Novozymes A/S, Bagsvaerd (DK)

(72) Inventors: Sara Landvik, Vedbaek (DK); Lars Henrik Oestergaard, Charlottenlund (DK); Lisbeth Kalum, Vaerloese (DK)

(73) Assignee: Novozymes A/S, Bagsvaerd (DK)

( * ) Notice: Subject to any disclaimer, the term of this patent is extended or adjusted under 35 U.S.C. 154(b) by 92 days.

(21) Appl. No.: 14/361,430

(22) PCT Filed: Nov. 28, 2012

(86) PCT No.: PCT/EP2012/073840
§ 371 (c)(1),
(2) Date: May 29, 2014

(87) PCT Pub. No.: WO2013/079533
PCT Pub. Date: Jun. 6, 2013

(65) Prior Publication Data
US 2014/0322770 A1 Oct. 30, 2014

(30) Foreign Application Priority Data
Dec. 2, 2011 (EP) .................................... 11191766

(51) Int. Cl.
| | | |
|---|---|---|
| *C12N 9/08* | (2006.01) |
| *C12P 7/04* | (2006.01) |
| *C12P 7/18* | (2006.01) |
| *C12P 7/22* | (2006.01) |
| *C12P 7/24* | (2006.01) |
| *C12P 7/26* | (2006.01) |
| *C12P 7/42* | (2006.01) |
| *C12P 7/64* | (2006.01) |
| *C12P 11/00* | (2006.01) |
| *C12P 13/00* | (2006.01) |
| *C11D 3/386* | (2006.01) |
| *C12P 13/02* | (2006.01) |

(52) U.S. Cl.
CPC .......... *C12N 9/0065* (2013.01); *C11D 3/38636* (2013.01); *C12P 7/04* (2013.01); *C12P 7/18* (2013.01); *C12P 7/22* (2013.01); *C12P 7/24* (2013.01); *C12P 7/26* (2013.01); *C12P 7/42* (2013.01); *C12P 7/64* (2013.01); *C12P 11/00* (2013.01); *C12P 13/008* (2013.01); *C12P 13/02* (2013.01); *Y02P 20/52* (2015.11)

(58) Field of Classification Search
None
See application file for complete search history.

(56) References Cited

FOREIGN PATENT DOCUMENTS

| WO | 2008/036061 A2 | 3/2008 | |
|---|---|---|---|
| WO | WO 2008036061 A2 * | 3/2008 | ............... A62D 3/02 |
| WO | 2011/120938 A2 | 10/2011 | |
| WO | 2012/068236 A2 | 5/2012 | |

OTHER PUBLICATIONS

GenBank Accession No. XP_001390900.2, published Mar. 3, 2011.*
Berka et al., Nature Biotechnology, vol. 29, No. 10, pp. 922-927 (2011).
Berka et al., UniProt Accession No. G2QID2 (2011).

* cited by examiner

*Primary Examiner* — Robert Mondesi
*Assistant Examiner* — Richard Ekstrom
(74) *Attorney, Agent, or Firm* — Elias Lambiris

(57) ABSTRACT

The present invention relates to isolated polypeptides having peroxygenaseactivity, and polynucleotides encoding the polypeptides. The invention also relates to nucleic acid constructs, vectors, and host cells comprising the polynucleotides as well as methods of producing and using the polypeptides.

24 Claims, No Drawings

US 9,404,093 B2

POLYPEPTIDES HAVING PEROXYGENASE ACTIVITY AND POLYNUCLEOTIDES ENCODING SAME

CROSS-REFERENCE TO RELATED APPLICATIONS

This application is a 35 U.S.C. 371 national application of PCT/EP2012/073840 filed Nov. 28, 2012, which claims priority or the benefit under 35 U.S.C. 119 of European application no. 11191766.2 filed Dec. 2, 2011, the contents of which are fully incorporated herein by reference.

REFERENCE TO A SEQUENCE LISTING

This application contains a Sequence Listing in computer readable form, which is incorporated herein by reference.

BACKGROUND

1. Field of the Invention

The present invention relates to polypeptides having peroxygenase activity, and polynucleotides encoding the polypeptides. The invention also relates to nucleic acid constructs, vectors, and host cells comprising the polynucleotides as well as methods of producing and using the polypeptides.

2. Description of the Related Art

WO 2006/034702 A1 discloses methods for the enzymatic hydroxylation of non-activated hydrocarbons, such as, naphtalene, toluol and cyclohexane, using the AaP peroxygenase enzyme of *Agrocybe aegerita* TM A1. This is also described in Ullrich and Hofrichter, 2005, FEBS Letters 579: 6247-6250.

DE 103 32 065 A1 discloses methods for the enzymatic preparation of acids from alcohols through the intermediary formation of aldehydes by using the AaP peroxygenase enzyme of *Agrocybe aegerita* TM A1.

A method was reported for the rapid and selective spectrophotometric direct detection of aromatic hydroxylation by the AaP peroxygenase (Kluge et al., 2007, Appl Microbiol Biotechnol 75: 1473-1478).

Another peroxygenase capable of aromatic peroxygenation was isolated from the coprophilous fungus *Coprinus radians* and characterized, the N-terminal 16 amino acids were identified and aligned with the N-terminal 14 amino acids of the AaP enzyme of the *A. aegerita* strain earlier published; but the encoding gene was not isolated (Anh et al., 2007, Appl Env Microbiol 73(17): 5477-5485).

WO 2008/119780 discloses several different peroxygenase polypeptides and their encoding polynucleotides, as well as recombinant production thereof.

WO 2011/120938 discloses site-specific hydroxylation of aliphatic hydrocarbons using peroxygenase polypeptides.

The present invention provides novel polypeptides having peroxygenase activity and polynucleotides encoding the polypeptides.

SUMMARY OF THE INVENTION

The present invention relates to isolated polypeptides having peroxygenase activity selected from the group consisting of:
(a) a polypeptide having at least 60% sequence identity to the mature polypeptide of SEQ ID NO: 2;
(b) a polypeptide encoded by a polynucleotide that hybridizes under medium stringency conditions with (i) the mature polypeptide coding sequence of SEQ ID NO: 1, (ii) the cDNA sequence thereof, or (iii) the full-length complement of (i) or (ii);
(c) a polypeptide encoded by a polynucleotide having at least 60% sequence identity to the mature polypeptide coding sequence of SEQ ID NO: 1, or the cDNA sequence thereof;
(d) a variant of the mature polypeptide of SEQ ID NO: 2 comprising a substitution, deletion, and/or insertion at one or more (e.g., several) positions; and
(e) a fragment of the polypeptide of (a), (b), (c), or (d) that has peroxygenase activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to methods of using the polypeptides of the invention.

DEFINITIONS

Peroxygenase: The term "peroxygenase" means an "unspecific peroxygenase" activity according to EC 1.11.2.1, that catalyzes insertion of an oxygen atom from $H_2O_2$ into a variety of substrates, such as nitrobenzodioxole. For purposes of the present invention, peroxygenase activity is determined according to the procedure described in Example 3, or in M. Poraj-Kobielska, M. Kinne, R. Ullrich, K. Scheibner, M. Hofrichter, "A spectrophotometric assay for the detection of fungal peroxygenases", *Analytical Biochemistry* (2011), doi: 10.1016/j.ab.2011.10.009 (see also *Analytical Biochemistry* (2012), vol. 421, issue 1, pp. 327-329).

In one aspect, the polypeptides of the present invention have at least 20%, e.g., at least 40%, at least 50%, at least 60%, at least 70%, at least 80%, at least 90%, at least 95%, or at least 100% of the peroxygenase activity of the mature polypeptide of SEQ ID NO: 2.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or domain; wherein the fragment has peroxygenase activity. In one aspect, a fragment contains at least 230 amino acid residues (e.g., amino acids 1 to 230 of SEQ ID NO: 2, or amino acids 20 to 230 of SEQ ID NO: 2), at least 240 amino acid residues (e.g., amino acids 1 to 240 of SEQ ID NO: 2, or amino acids 20 to 240 of SEQ ID NO: 2), or at least 250 amino acid residues (e.g., amino acids 1 to 250 of SEQ ID NO: 2, or amino acids 20 to 250 of SEQ ID NO: 2).

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 18 to 259 of SEQ ID NO: 2, based on the SignalP 3.0 program, that predicts amino acids 1 to 17 of SEQ ID NO: 2 is a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having peroxygenase activity. In one aspect, the mature polypeptide coding sequence is nucleotides 52 to 100, 145 to 385, 444 to 712, and 759 to 925 of SEQ ID NO: 1, or the cDNA sequence thereof, based on the SignalP 3.0 program that predicts nucleotides 1 to 51 of SEQ ID NO: 1 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having peroxygenase activity. In one aspect, a subsequence contains at least 690 nucleotides, at least 720 nucleotides, or at least 750 nucleotides.

Variant: The term "variant" means a polypeptide having peroxygenase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

DETAILED DESCRIPTION

Polypeptides Having Peroxygenase Activity

In an embodiment, the present invention relates to isolated polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peroxygenase activity. In one aspect, the polypeptides differ by no more than 10 amino acids, e.g., 1, 2, 3, 4, 5, 6, 7, 8, or 9, from the mature polypeptide of SEQ ID NO: 2.

A polypeptide of the present invention preferably comprises or consists of the amino acid sequence of SEQ ID NO: 2, or an allelic variant thereof; or is a fragment thereof having peroxygenase activity. In another aspect, the polypeptide comprises or consists of the mature polypeptide of SEQ ID NO: 2. In another aspect, the polypeptide comprises or consists of amino acids 1 to 259 of SEQ ID NO: 2, or amino acids 20 to 259 of SEQ ID NO: 2

The polypeptides of the invention may comprise the amino acid sequence shown as:
Glu-His-Asp-Gly-Ser-Leu-Ser-Arg (SEQ ID NO: 3),
Glu-His-Asp-Ala-Ser-Leu-Ser-Arg (SEQ ID NO: 4),
Glu-His-Asp-Gly-Ser-Ile-Ser-Arg (SEQ ID NO: 5), or
Glu-His-Asp-Ala-Ser-Ile-Ser-Arg (SEQ ID NO: 6).
which corresponds to amino acids 108-115 of SEQ ID NO: 2, and which coordinates a Mn atom next to the heme group.

Thus, the amino acid sequence of the polypeptides of the invention may comprise the motif shown as (which is the result of combining SEQ ID NO: 3 to SEQ ID NO: 6): E-H-D-[G,A]-S-[L,I]-S—R (SEQ ID NO: 7).

The polypeptides of the invention may comprise the amino acid sequence shown as:
Arg-Gly-Pro-Cys-Pro-Xaa-Met-Asn-Ser-Leu (SEQ ID NO: 10),
Arg-Ala-Pro-Cys-Pro-Xaa-Met-Asn-Ser-Leu (SEQ ID NO: 11),
Arg-Gly-Pro-Cys-Pro-Xaa-Leu-Asn-Ser-Leu (SEQ ID NO: 12),
Arg-Ala-Pro-Cys-Pro-Xaa-Leu-Asn-Ser-Leu (SEQ ID NO: 13),
Arg-Gly-Pro-Cys-Pro-Xaa-Met-Asn-Thr-Leu (SEQ ID NO: 14),
Arg-Ala-Pro-Cys-Pro-Xaa-Met-Asn-Thr-Leu (SEQ ID NO: 15),
Arg-Gly-Pro-Cys-Pro-Xaa-Leu-Asn-Thr-Leu (SEQ ID NO: 16), or
Arg-Ala-Pro-Cys-Pro-Xaa-Leu-Asn-Thr-Leu (SEQ ID NO: 17);
which corresponds to amino acids 35-44 of SEQ ID NO: 2, and which form essential structural elements linked to the heme group. Xaa can be any amino acid, but preferably it is Met, Gly, Ala, or Val.

Thus, the amino acid sequence of the polypeptides of the invention may comprise the motif shown as (which is the result of combining SEQ ID NO: 10 to SEQ ID NO: 17):
R-[G,A]-P-C-P-X-[M,L]-N-[S,T]-L (SEQ ID NO: 18); and preferably
R-[G,A]-P-C-P-[M,G,A,V]-[M,L]-N-[S,T]-L.

In another embodiment, the present invention relates to an isolated polypeptide having peroxygenase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, (ii) the cDNA sequence thereof, or (iii) the full-length complement of (i) or (ii) (Sambrook et al., 1989, *Molecular Cloning, A Laboratory Manual*, 2d edition, Cold Spring Harbor, N.Y.).

The polynucleotide of SEQ ID NO: 1, or a subsequence thereof, as well as the polypeptide of SEQ ID NO: 2, or a fragment thereof, may be used to design nucleic acid probes to identify and clone DNA encoding polypeptides having peroxygenase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having peroxygenase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art. In one aspect, the nucleic acid probe is nucleotides 366 to 385 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1, or the cDNA sequence thereof.

In another embodiment, the present invention relates to an isolated polypeptide having peroxygenase activity encoded by a polynucleotide having a sequence identity to the mature polypeptide coding sequence of SEQ ID NO: 1 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for peroxygenase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Peroxygenase Activity

A polypeptide having peroxygenase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide, such as a polypeptide from a fungus in the family Trichocomaceae. For example, the polypeptide may be an *Aspergillus* polypeptide, such as an *Aspergillus carbonarius*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, or *Aspergillus oryzae* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP),

*Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus nigerglucoamylase, Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (*Praha*) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is an *Aspergillus* cell. In a more preferred aspect, the cell is an *Aspergillus carbonarius* cell.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an anti-nutritive factor.

The transgenic plant can be dicotyledonous (a dicot) or monocotyledonous (a monocot).

Examples of monocot plants are grasses, such as meadow grass (blue grass, *Poa*), forage grass such as *Festuca, Lolium,* temperate grass, such as *Agrostis,* and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Removal or Reduction of Peroxygenase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having peroxygenase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (sRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO: 1 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially peroxygenase-free product is of particular interest in the production of eukaryotic polypeptides, in particular fungal proteins such as enzymes. The peroxygenase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from peroxygenase activity that is produced by a method of the present invention.

Compositions

The peroxygenase polypeptides of the invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the invention as described herein.

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art.

The detergent additive as well as the detergent composition may comprise one or more additional enzymes such as a protease, lipase, cutinase, amylase, carbohydrase, cellulase, pectinase, mannanase, arabinase, galactanase, xylanase, oxidase, e.g., a laccase, and/or peroxidase.

The polypeptide of the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

The polypeptide having peroxygenase activity (the peroxygenase), and optionally also a source of hydrogen peroxide, may be formulated as a liquid (e.g. aqueous), a solid, a gel, a paste or a dry product formulation. The dry product formulation may subsequently be re-hydrated to form an active liquid or semi-liquid formulation usable in the methods of the invention.

When the peroxygenase and the source of hydrogen peroxide are formulated as a dry formulation, the components may be mixed, arranged in discrete layers or packaged separately.

When other than dry form formulations are used, and even in that case, it is preferred to use a two-part formulation system having the peroxygenase separate from the source of hydrogen peroxide.

The composition of the invention may further comprise auxiliary agents such as wetting agents, thickening agents, buffer(s) for pH control, stabilisers, perfume, colourants, fillers and the like.

Useful wetting agents are surfactants, i.e. non-ionic, anionic, amphoteric or zwitterionic surfactants. Surfactants are further described above.

Methods and Uses

The peroxygenase polypeptides of the invention may be used for site specific hydroxylation in position 2 or position 3 of an aliphatic hydrocarbon. The aliphatic hydrocarbon must include a chain of at least 3 carbons, and either (one or more) end of the aliphatic hydrocarbon may be used as the starting point to determine which carbon is in position 2 or 3. The aliphatic hydrocarbon must have at least one hydrogen attached to the carbon (which is hydroxylated) in position 2 or 3. In a preferred embodiment, the carbon in position 2 or 3, which is hydroxylated with the peroxygenase, is unsubstituted (before the hydroxylation is carried out).

Accordingly, in a first aspect, the present invention provides a method for hydroxylation in position 2 or 3 of either end (one or more ends) of a substituted or unsubstituted, linear or branched, aliphatic hydrocarbon having at least 3 carbons and having a hydrogen attached to the carbon in position 2 or 3, comprising contacting the aliphatic hydrocarbon with hydrogen peroxide and a polypeptide having peroxygenase activity of the invention.

The method of the invention may be used for a variety of purposes, like bulk chemical synthesis (biocatalysis), increasing aqueous solubility of aliphatic hydrocarbons, bioremediation, and modification of the characteristics of food products.

The method of the invention may also be used for a number of industrial processes in which said hydroxylation reactions are beneficial. An example of such use is in the manufacture of pulp and paper products where alkanes and other relevant aliphatic hydrocarbons that are present in the wood (resin) can result in depositioning problems in the pulp and paper manufacturing process. These hydrophobic compounds are the precursors of the so-called pitch deposits within the pulp and paper manufacturing processes. Pitch deposition results in low quality pulp, and can cause the shutdown of pulp mill operations. Specific issues related to pulps with high extractives content include runnability problems, spots and holes in the paper, and sheet breaks. Treatment with peroxygenase can increase the solubility of said compounds and thereby mitigate problems.

Yet another use of the method of the invention is in i.e. oil or coal refineries where the peroxygenase catalyzed hydroxylation can be used to modify the solubility, viscosity and/or combustion characteristics of hydrocarbons. Specifically the treatment can lead to changes in the smoke point, the kindling point, the fire point and the boiling point of the hydrocarbons subjected to the treatment.

In the synthesis of bulk chemicals, agro chemicals (incl. pesticides), specialty chemicals and pharmaceuticals the method of the invention may obviously be relevant in terms of selectively introducing hydroxy groups in the substrates thereby affecting the solubility of the modified compound. Furthermore, the selective hydroxylation provides a site for further modification by methods known in the art of organic chemical synthesis and chemo-enzymatic synthesis.

Natural gas is extensively processed to remove higher alkanes. Hydroxylation of such higher alkanes may be used to improve water solubility, and thus facilitate removal of the higher alkanes by washing the natural gas stream. Removal may be performed at the well or during refining.

Hydroxylation of oil waste will significantly improve biodegradability and will be applicable both in connection with waste water treatment from refineries and bioremediation of contaminated ground or water In a second aspect, the present invention provides a method for hydroxylation in position 2 or 3 of the terminal end of an acyl group of a lipid, comprising contacting the lipid with hydrogen peroxide and a polypeptide having peroxygenase activity of the invention.

Hydroxylation of the acyl group of a lipid generally improves the aqueous solubility of the lipid. Accordingly, the method of the invention may be used to remove or reduce oil or lipid containing stains, like chocolate, from laundry, by contacting the laundry with a peroxygenase and a source of hydrogen peroxide, and optionally a surfactant.

In another aspect, the methods of the invention may be used to reduce unpleasant odors from laundry by contacting the laundry with a peroxygenase and a source of hydrogen peroxide, and optionally a surfactant. The method of the invention results in reduction of the amount of butanoic acid (butyric acid) in the laundry. Butanoic acid is formed during washing of laundry when certain animal fats and plant oils are hydrolyzed, e.g. by detergent lipase, to yield free fatty acids, including butanoic acid. Butanoic acid has an extremely unpleasant odor. The peroxygenase hydroxylates the butanoic acid to 2-hydroxybutyric acid (alpha-hydroxybutyric acid) or 3-hydroxybutyric acid (beta-hydroxybutyric acid).

The present invention also provides a method for site specific introduction of a hydroxy and/or an oxo (keto) group at the second or third carbon of at least two ends of an aliphatic hydrocarbon, using a peroxygenase polypeptide of the invention, and hydrogen peroxide.

The aliphatic hydrocarbon must include a chain of at least five carbons. The second and third carbons are determined by counting the carbon atoms from any end of the aliphatic hydrocarbon.

The aliphatic hydrocarbon must have at least one hydrogen attached to a carbon which is hydroxylated by attachment of a hydroxy group; and at least two hydrogens attached to a carbon when an oxo group is introduced. In a preferred embodiment, the second or third carbon is unsubstituted before being contacted with the peroxygenase.

According to the method of the invention, the hydroxy and/or oxo groups are introduced independently of each other at the (at least) two ends of the aliphatic hydrocarbon. Thus, a hydroxy group can be introduced at one end, at the same time as an oxo group is introduced at another (the other) end—and vice versa. Two hydroxy groups, or two oxo groups, or one hydroxy group and one oxo group, cannot be introduced at the same end of the aliphatic hydrocarbon.

In the context of the present invention, "oxidation" means introduction of a hydroxy and/or an oxo group.

Accordingly, in a first aspect, the present invention provides a method for introducing a hydroxy and/or an oxo (keto) group at the second or third carbon of (at least) two ends of a substituted or unsubstituted, linear or branched, aliphatic hydrocarbon having at least five carbons and having at least one hydrogen attached to said second or third carbon, comprising contacting the aliphatic hydrocarbon with hydrogen peroxide and a polypeptide having peroxygenase activity of the invention.

In a preferred embodiment, the aliphatic hydrocarbon is oxidized to (converted to) a diol, by introduction of two hydroxy groups. More preferably, the two hydroxy groups are located at each end of a linear aliphatic hydrocarbon.

The method of the invention may be used for a variety of purposes, like bulk chemical synthesis (biocatalysis), increasing aqueous solubility of aliphatic hydrocarbons, bioremediation, and modification of the characteristics of food products.

The method of the invention may also be used for a number of industrial processes in which said oxidation reactions are beneficial. An example of such use is in the manufacture of pulp and paper products where alkanes and other relevant aliphatic hydrocarbons that are present in the wood (resin) can result in depositioning problems in the pulp and paper manufacturing process. These hydrophobic compounds are the precursors of the so-called pitch deposits within the pulp and paper manufacturing processes. Pitch deposition results in low quality pulp, and can cause the shutdown of pulp mill operations. Specific issues related to pulps with high extractives content include runnability problems, spots and holes in the paper, and sheet breaks. Treatment with peroxygenase can increase the solubility of said compounds and thereby mitigate problems.

Yet another use of the method of the invention is in, for example, oil or coal refineries where the peroxygenase catalyzed oxidation can be used to modify the solubility, viscosity and/or combustion characteristics of hydrocarbons. Specifically the treatment can lead to changes in the smoke point, the kindling point, the fire point and the boiling point of the hydrocarbons subjected to the treatment.

In the synthesis of bulk chemicals, agro chemicals (incl. pesticides), specialty chemicals and pharmaceuticals the method of the invention may obviously be relevant in terms of selectively introducing hydroxy groups in the substrates thereby affecting the solubility of the modified compound. Furthermore, the selective oxidation provides a site for further modification by methods known in the art of organic chemical synthesis and chemo-enzymatic synthesis.

Natural gas is extensively processed to remove higher alkanes. Oxidation of such higher alkanes may be used to improve water solubility, and thus facilitate removal of the higher alkanes by washing the natural gas stream. Removal may be performed at the well or during refining.

Oxidation, according to the invention, of oil waste will significantly improve biodegradability and will be applicable both in connection with waste water treatment from refineries and bioremediation of contaminated ground or water The methods of the invention may be carried out with an immobilized peroxygenase polypeptide of the invention.

The methods of the invention may be carried out in an aqueous solvent (reaction medium), various alcohols, ethers, other polar or non-polar solvents, or mixtures thereof. By studying the characteristics of the aliphatic hydrocarbon used in the methods of the invention, suitable examples of solvents are easily recognized by one skilled in the art. By raising or lowering the pressure at which the hydroxylation/oxidation is carried out, the solvent (reaction medium) and the aliphatic hydrocarbon can be maintained in a liquid phase at the reaction temperature.

The methods according to the invention may be carried out at a temperature between 0 and 90 degrees Celsius, preferably between 5 and 80 degrees Celsius, more preferably between 10 and 70 degrees Celsius, even more preferably between 15 and 60 degrees Celsius, most preferably between 20 and 50 degrees Celsius, and in particular between 20 and 40 degrees Celsius.

The methods of the invention may employ a treatment time of from 10 seconds to (at least) 24 hours, preferably from 1 minute to (at least) 12 hours, more preferably from 5 minutes to (at least) 6 hours, most preferably from 5 minutes to (at least) 3 hours, and in particular from minutes to (at least) 1 hour.

Diols (di-hydroxy aliphatic hydrocarbons) produced by the method of the invention may be used for producing polyurethan. Polyurethane is a polymer composed of a chain of organic units joined by carbamate (urethane) links. Polyurethane polymers are formed through step-growth polymerization, by reacting a monomer (with at least two isocyanate functional groups) with another monomer (with at least two hydroxyl groups) in the presence of a catalyst.

The present invention also provides a method for introducing an oxo (keto) group at the second or third carbon of a substituted or unsubstituted, linear or branched, aliphatic hydrocarbon having at least five carbons and having at least two hydrogens attached to said second or third carbon, comprising contacting the aliphatic hydrocarbon with hydrogen peroxide and a polypeptide having peroxygenase activity of the invention.

In yet another aspect, the present invention also provides a method for introducing a hydroxy or an oxo group at a terminal carbon of a linear or branched aliphatic hydrocarbon having at least five carbons, which is substituted with a carboxy group, comprising contacting the aliphatic hydrocarbon with hydrogen peroxide and a polypeptide having peroxygenase activity of the invention.

In an embodiment, the aliphatic hydrocarbon which is substituted with a carboxy group is a fatty acid; preferably butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachidic acid), linoleic acid, linolenic acid, arachidonic acid, eicosapentaenoic acid, or docosahexaenoic acid.

In yet another aspect, the present invention also provides a method for changing (oxidizing) a primary alcohol of a linear or branched aliphatic hydrocarbon having at least five carbons to the corresponding acid, comprising contacting the alcohol of an aliphatic hydrocarbon with hydrogen peroxide and a polypeptide having peroxygenase activity of the invention.

For example, pentanol may be changed (oxidized) to pentanoic acid (valeric acid), hexanol may be changed to hexanoic acid (caproic acid), heptanol may be changed to heptanoic acid (enanthic acid), octanol may be changed to octanoic acid (caprylic acid), nonanol may be changed to nonanoic acid (pelargonic acid), decanol may be changed to decanoic acid (capric acid), dodecanol may be changed to dodecanoic acid (lauric acid), tetradecanol may be changed to tetradecanoic acid (myristic acid), hexadecanol may be changed to hexadecanoic acid (palmitic acid), octadecanol may be changed to octadecanoic acid (stearic acid), and eicosanol may be changed to eicosanoic acid (arachidic acid).

The polypeptides having peroxygenase activity of the invention (peroxygenase polypeptides or peroxygenases) are used in the methods of the invention in an amount of 0.005-50 ppm (mg/l), or 0.01-40, 0.02-30, 0.03-25, 0.04-20, 0.05-15, 0.05-10, 0.05-5, 0.05-1, 0.05-0.8, 0.05-0.6, or 0.1-0.5 ppm. The amount of enzyme refers to mg of a well-defined enzyme preparation.

In the methods of the invention, the peroxygenase may be applied alone or together with an additional enzyme. The term "an additional enzyme" means at least one additional enzyme, e.g. one, two, three, four, five, six, seven, eight, nine, ten or even more additional enzymes.

The term "applied together with" (or "used together with") means that the additional enzyme may be applied in the same, or in another step of the method of the invention. The other process step may be upstream or downstream, as compared to the step in which the peroxygenase is used.

In particular embodiments the additional enzyme is an enzyme which has protease, lipase, xylanase, cutinase, oxidoreductase, cellulase, endoglucanase, amylase, mannanase, steryl esterase, and/or cholesterol esterase activity. Examples of oxidoreductase enzymes are enzymes with laccase, and/or peroxidase activity.

The term "a step" of a method means at least one step, and it could be one, two, three, four, five or even more method steps. In other words the peroxygenases of the invention may be applied in at least one method step, and the additional enzyme(s) may also be applied in at least one method step, which may be the same or a different method step as compared to the step where the peroxygenase is used.

The term "enzyme preparation" means a product containing at least one peroxygenase. The enzyme preparation may also comprise enzymes having other enzyme activities. In addition to the enzymatic activity, such a preparation preferably contains at least one adjuvant. Examples of adjuvants are buffers, polymers, surfactants and stabilizing agents.

Hydrogen Peroxide

The hydrogen peroxide (or source of hydrogen peroxide) required by the peroxygenase may be provided as an aqueous solution of hydrogen peroxide or a hydrogen peroxide precursor for in situ production of hydrogen peroxide. Any solid entity which liberates upon dissolution a peroxide which is useable by peroxygenase can serve as a source of hydrogen peroxide. Compounds which yield hydrogen peroxide upon dissolution in water or an appropriate aqueous based medium include but are not limited to metal peroxides, percarbonates, persulphates, perphosphates, peroxyacids, alkyperoxides, acylperoxides, peroxyesters, urea peroxide, perborates and peroxycarboxylic acids or salts thereof.

Another source of hydrogen peroxide is a hydrogen peroxide generating enzyme system, such as an oxidase together with a substrate for the oxidase. Examples of combinations of oxidase and substrate comprise, but are not limited to, amino acid oxidase (see e.g. U.S. Pat. No. 6,248,575) and a suitable amino acid, glucose oxidase (see e.g. WO 95/29996) and glucose, lactate oxidase and lactate, galactose oxidase (see e.g. WO 00/50606) and galactose, and aldose oxidase (see e.g. WO 99/31990) and a suitable aldose.

By studying EC 1.1.3._, EC 1.2.3._, EC 1.4.3._, and EC 1.5.3._ or similar classes (under the International Union of Biochemistry), other examples of such combinations of oxidases and substrates are easily recognized by one skilled in the art.

Hydrogen peroxide or a source of hydrogen peroxide may be added at the beginning of or during the method of the invention, e.g. as one or more separate additions of hydrogen peroxide; or continously as fed-batch addition. Typical amounts of hydrogen peroxide correspond to levels of from 0.001 mM to 25 mM, preferably to levels of from 0.005 mM to 5 mM, and particularly to levels of from 0.01 to 1 mM hydrogen peroxide. Hydrogen peroxide may also be used in an amount corresponding to levels of from 0.1 mM to 25 mM, preferably to levels of from 0.5 mM to 15 mM, more preferably to levels of from 1 mM to 10 mM, and most preferably to levels of from 2 mM to 8 mM hydrogen peroxide.

Aliphatic Hydrocarbons

The hydrocarbons, which are hydroxylated in the method of the invention, are aliphatic hydrocarbons having a chain of at least 3 carbons, and having a hydrogen attached to the carbon in position 2 or 3. Preferably, the aliphatic hydrocarbon is an alkane or an alkene; more preferably, the aliphatic hydrocarbon is an alkane, such as propane, butane, pentane, hexane, heptane, octane, nonane or decane, or isomers thereof.

The aliphatic hydrocarbons are linear or branched, but not cyclic, as site specific hydroxylation is not possible with cyclic hydrocarbons. Branched hydrocarbons correspond to isomers of linear hydrocarbons.

The aliphatic hydrocarbons are substituted or unsubstituted. Preferably, the aliphatic hydrocarbons are unsubstituted, such as non-activated hydrocarbons.

When the aliphatic hydrocarbons are substituted (functional groups attached), the preferred substituents are halogen, hydroxyl, carboxyl, amino, nitro, cyano, thiol, sulphonyl, formyl, acetyl, methoxy, ethoxy, phenyl, benzyl, xylyl, carbamoyl and sulfamoyl; more preferred substituents are chloro, hydroxyl, carboxyl and sulphonyl; and most preferred substituents are chloro and carboxyl.

The aliphatic hydrocarbons may be substituted by up to 10 substituents, up to 8 substituents, up to 6 substituents, up to 4 substituents, up to 2 substituents, or by up to one substituent.

In a preferred embodiment, the aliphatic hydrocarbon is a fatty acid (the substituent is a carboxyl group). Examples of fatty acids include, but are not limited to, butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachidic acid), linoleic acid, linolenic acid, arachidonic acid, eicosapentaenoic acid, and docosahexaenoic acid.

In a second aspect, the aliphatic hydrocarbon is an acyl group of a lipid, such as a monoglyceride, diglyceride, triglyceride, phospholipid or sphingolipid; and the hydroxylation takes place in position 2 or position 3 of the terminal end of the acyl group. The acyl group must have at least one hydrogen attached to the carbon in position 2 or 3 of the terminal end. The acyl group may be saturated or unsaturated, and optionally functional groups (substituents) may be attached. Examples of acyl groups include, but are not limited to, the acyl forms of butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachidic acid), linoleic acid, linolenic acid, arachidonic acid, eicosapentaenoic acid, and docosahexaenoic acid.

Signal Peptide

The present invention also relates to an isolated polynucleotide encoding a signal peptide comprising or consisting of amino acids 1 to 17 of SEQ ID NO: 2. The polynucleotides may further comprise a gene encoding a protein, which is operably linked to the signal peptide. The protein is preferably foreign to the signal peptide. In one aspect, the polynucleotide encoding the signal peptide is nucleotides 1 to 51 of SEQ ID NO: 1.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The present invention is further described by the following examples that should not be construed as limiting the scope of the invention.

EXAMPLES

Strains

*Aspergillus oryzae* MT3568 is an amdS (acetamidase) disrupted gene derivative of *Aspergillus oryzae* JaL355 (WO 2002/40694), in which pyrG auxotrophy was restored by disrupting the *A. oryzae* acetamidase (amdS) gene with the pyrG gene. Protoplasts of *Aspergillus oryzae* MT3568 were prepared according to WO 95/002043 ("Transformation of *Aspergillus oryzae* or *Aspergillus niger*"), but using Glucanex (which is identical to Lysing Enzyme, Sigma L1412) instead of Novozym® 234.

Media and Solutions

DAP-4C-1 Medium 11 g $MgSO_4$, $7H_2O$ 1.0 g $KH_2PO_4$ 2.0 g Citric acid ($C_6H_8O_7$, $H_2O$)

20 g Dextrose 10 g Maltose 5.2 g $K_3PO_4$, $H_2O$ 0.5 g Yeast Extract 0.5 ml KU6 Trace metal solution (AMG, MSA-SUB-FS-0042)

Mix until completely solved 1 ml Dowfax 63N10 (linear EO/PO block copolymers, defoam/antifoam agent) is added Adjust volume with Milli-Q-water up to 1000 ml $CaCO_3$ tablets á 0.5 g (add 1 tablet per 200 ml)

Before inoculation, each shake flask á 150 ml is added 3.5 ml of 50% di-ammoniumhydrogenphosphat (($NH_4)_2HPO_4$), and 5.0 ml of 20% lactic acid.

KU6 Trace Metal Solution (AMG, MSA-SUB-FS-0042)

6.8 g $ZnCl_2$ 2.5 g $CuSO_4$, $5H_2O$ 0.13 g Nickel Chloride anhydrous 13.9 g $FeSO_4$, $7H_2O$ 8.45 g $MnSO_4$, $H_2O$ 3.0 g Citric acid ($C_6H_8O_7$, $H_2O$)

Ion exchanged water up to 1000 ml

TABLE 1

KU6 trace metal solution.

| Raw material | Chem. formula | Supplier | 7-cif. no. | Amount |
|---|---|---|---|---|
| Zinc Chloride | $ZnCl_2$ | Merck 108816 | 102-4965 | 6.8 g |
| Copper Sulfate | $CuSO_4$, $5H_2O$ | Merck 102790 | 109-0771 | 2.5 g |
| Nickel Chloride anhydrous | $NiCl_2$ | Merck 806722 | 101-6652 | 0.13 g |
| Iron Sulfate | $FeSO_4$, $7H_2O$ | Merck 103965 | | 13.9 g |
| Manganese Sulfate | $MnSO_4$, $H_2O$ | Merck 105941 | | 8.45 g |
| Citric acid | $C_6H_8O_7$, $H_2O$ | Merck 100244 | | 3.0 g |
| Ion exchanged water up to | | | | 1000 ml |

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, and 10 g of sodium chloride, and deionized water to 1 liter.

COVE sucrose plates were composed of 342 g of sucrose, 20 g of agar powder, 20 ml of COVE salt solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, Triton X-100 (50 µl/500 ml) were added.

COVE salt solution was composed of 26 g of $MgSO_4$, $7H_2O$, 26 g of KCL, 26 g of $KH_2PO_4$, 50 ml of COVE trace metal solution, and deionized water to 1 liter.

COVE trace metal solution was composed of 0.04 g of $Na_2B_4O_7$, $10H_2O$, 0.4 g of $CuSO_4$, $5H_2O$, 1.2 g of $FeSO_4$, $7H_2O$, 0.7 g of $MnSO_4$, $H_2O$, 0.8 g of $Na_2Moa_4$, $2H_2O$, 10 g of $ZnSO_4$, $7H_2O$, and deionized water to 1 liter

Example 1

Expression of a Peroxygenase from Aspergillus carbonarius

The polynucleotide of SEQ ID NO: 1, encoding a peroxygenase from *Aspergillus carbonarius* was amplified by PCR. The PCR was composed of 1 µl of genomic DNA of *Aspergillus carbonarius*, 0.75 µl of cloning primer forward (10 µM), 0.75 µl of primer cloning primer reverse (10 µM), 3 µl of 5×HF buffer (Finnzymes Oy, Finland), 0.25 µl of 50 mM $MgCl_2$, 0.30 µl of 10 mM dNTP, 0.15 µl of PHUSION® DNA polymerase (Finnzymes Oy, Finland), and 8.8 µl PCR-grade water.

The amplification reaction was performed using a Thermal Cycler programmed for 2 minutes at 98° C. followed by 30 cycles each consisting of 98° C. for 15 seconds, 60° C. for 30 seconds, and 72° C. for 90 seconds; and 3 minutes at 72° C.

```
Cloning primer forward (SEQ ID NO: 8):
5'-ACACAACTGGGGATCCACCATGAAGTCCACTATTCT

TCTTATTACCACCTCT-3'

Cloning primer reverse (SEQ ID NO: 9):
5'-AGATCTCGAGAAGCTTATCTTTGGTACTAATGGTCC

AGGCAAATAGT-3'
```

The PCR product was isolated on 1.0% agarose gel electrophoresis using TAE buffer where the PCR band was excised from the gel and purified using a GFX® PCR DNA and Gel Band Purification Kit (GE Healthcare, HiHerod, Denmark) according to manufacturer's instructions. DNA corresponding to the *Aspergillus carbonarius* peroxygenase gene (SEQ ID NO: 1) was cloned into the expression vector pDAu109 (WO 2005042735) previously linearized with Bam HI and Hind III, using an IN-FUSION™ Dry-Down PCR Cloning Kit (BD Biosciences, Palo Alto, Calif., USA) according to the manufacturer's instructions.

A 1 µl volume of the undiluted ligation mixture was used to transform *E. coli* TOP10 chemically competent cells (Invitrogen, Carlsbad, Calif., USA). Two colonies were selected on LB agar plates containing 100 µg of ampicillin per ml and cultivated overnight in 2 ml of LB medium supplemented with 100 µg of ampicillin per ml. Plasmid DNA was purified using a Jetquick Plasmid Miniprep Spin Kit (Genomed GmbH, Løhne, Germany) according to the manufacturer's instructions.

The *Aspergillus carbonarius* peroxygenase gene sequence was verified by Sanger sequencing before heterologous expression. A plasmid containing the nucleotide sequence of SEQ ID NO: 1 was selected for heterologous expression of the peroxygenase gene in an *Aspergillus oryzae* MT3568 host cell.

*Aspergillus oryzae* MT3568 strain was used for heterologous expression of the polynucleotide of SEQ ID NO: 1.

One hundred µl of *Aspergillus oryzae* MT3568 protoplasts were mixed with 1-2 µg of the *Aspergillus* expression vector containing the nucleotide sequence of SEQ ID NO: 1, and 250 µl of 60% PEG 4000 (Applichem, Darmstadt, Germany) (polyethylene glycol, molecular weight 4,000), 10 mM $CaCl_2$, and 10 mM Tris-HCl pH 7.5 and gently mixed. After 30 min of incubation at 37° C., 4 ml of topagar (temp. 40° C.) was added, and the protoplasts were spread onto COVE plates for selection. After incubation for 4-7 days at 37° C. spores of four transformants were inoculated into 0.5 ml of DAP-4C-01 medium in 96 deep well plates. After 4-5 days cultivation at 30° C., the culture broths were analyzed by SDS-PAGE to identify the transformants producing the largest amount of recombinant peroxygenase from *Aspergillus carbonarius*, and the culture broths were also analyzed in assays for confirmation of activity.

An *Aspergillus oryzae* transformant constructed as described above was fermented in 150 ml DAP-4C-01 medium in 500 ml fluted shake flasks incubated at 26° C. to 30° C. in a shaking platform incubator rotating at 150 RPM for 5 days and further used for assays as described below.

Example 2

Oxidation of 2,2'-azino-bis(3-ethylbenzthiazoline-6-sulfonic acid)

Peroxygenases oxidize 2,2'-azino-bis(3-ethylbenzthiazoline-6-sulfonic acid), also known as ABTS, in the presence of hydrogen peroxide and the produced green color is quantified spectrophotometrically at 405 nm ($\epsilon_{405}$=36,800 $M^{-1}$ $cm^{-1}$).

The reaction mixture (0.2 ml) contained 1.0 mM ABTS, 20 µl peroxygenase fermentation supernatant (see Example 1), 0.5 mM hydrogen peroxide, and 50 mM Britton-Robinson buffer pH 4.

The reaction was started by adding the peroxygenase fermentation supernatant to the other ingredients used in the assay. A SpectraMax microtitre plate reader from Molecular Devices was applied to monitor the change in absorbance at 405 nm in a 96 well microtitre plate at room temperature. Blanks prepared without addition of enzyme were included.

The increase in absorbance was recorded over 5 minutes and the results are shown in Table 2 as change in absorbance (milli Abs) pr. minute.

TABLE 2

| Sample | Rate (mA/min) at pH 4 |
|---|---|
| Blank | 0.2 |
| Peroxygenase from Example 1 | 83.5 |

Example 3

Oxidation of Nitrobenzodioxole

Peroxygenases oxidize nitrobenzodioxole (1,2-(Methylenedioxy)-4-nitrobenzene) to nitrocatechol in the presence of hydrogen peroxide and the produced yellow color is quantified spectrophotometrically at 425 nm ($\epsilon_{425}$=9,700 $M^{-1}$ $cm^{-1}$).

A 10 mM stock solution of nitrobenzodioxole (98% pure, 161500 Aldrich) was prepared in acetonitrile. The final reaction mixture (0.2 ml) contained 1.0 mM nitrobenzodioxole, 10% acetonitrile, 20 µl peroxygenase fermentation supernatant (see Example 1), 0.5 mM hydrogen peroxide, and 50 mM phosphate buffer pH 7.

The reaction was started by adding the peroxygenase fermentation supernatant to the other ingredients used in the assay. A SpectraMax microtitre plate reader from Molecular Devices was applied to monitor the change in absorbance at 425 nm in a 96 well microtitre plate at room temperature. Blanks prepared without addition of enzyme were included.

The increase in absorbance was recorded over 5 minutes and the results are shown in Table 3 as change in absorbance (milli Abs) pr. minute.

TABLE 3

| Sample | Rate (mA/min) at pH 7 |
| --- | --- |
| Blank | −1.1 |
| Peroxygenase from Example 1 | 35.8 |

Example 4

Oxidation of Naphthalene

Oxidation of 1 mM naphthalene with 1 mM $H_2O_2$ was carried out with 20% acetonitrile and 5 mM phosphate buffer at pH 6.5, using 0.01 mg/mL of purified peroxygenase (mature peroxygenase encoded by SEQ ID NO: 1) in a total reaction volume of 1 mL. Reaction was performed at room temperature for 25 minutes and stopped by adding 50 µL of 50% (w/v) trichloroacetic acid.

Sample was analyzed on an Agilent 1200 HPLC system equipped with a Diode Array Detector (Agilent, Santa Clara Calif., USA) and separated on a Gemini C6-Phenyl (110 Å, 2×150 mm, 3 µm) column from Phenomenex (Torrance Calif., USA) thermostated at 40° C. Two mobile phases were used: (A) 0.1% formic acid, and (B) 0.1% formic acid in acetonitrile.

Separation was run using stepwise gradient starting with 30% B held for 0.5 min, then increasing to 50% B within 3.5 min and then increasing to 60% B within 5 min with a constant flow rate of 0.4 mL/min.

Naphthalene and its possible oxidation products, 1-naphthol, 2-naphthol, 1,4-naphthoquinone, were identified and quantified by external calibration using authentic standards, based on their retention times, UV absorbtion spectra (210 nm).

The peroxygenase oxidised naphthalene yielding a single product, 1-naphthol (3.6%).

Example 5

Oxidation of Dibenzothiophene

Oxidation of 1 mM dibenzothiophene with 1 mM $H_2O_2$ was carried out with 30% acetonitrile and 5 mM phosphate buffer at pH 6.5, using 0.01 mg/mL of purified peroxygenase (mature peroxygenase encoded by SEQ ID NO: 1) in a total reaction volume of 1 mL. Reaction was performed at room temperature for 25 minutes, and stopped by adding 50 µL of 50% (w/v) trichloroacetic acid.

Sample was analyzed on an Agilent 1200 HPLC system equipped with a Diode Array Detector (Agilent, Santa Clara Calif., USA) and separated on a Gemini C6-Phenyl (110 Å, 2×150 mm, 3 µm) column from Phenomenex (Torrance Calif., USA) thermostated at 40° C. Two mobile phases were used: (A) 0.1% formic acid, and (B) 0.1% formic acid in acetonitrile.

Separation was run using stepwise gradient starting with 30% B held for 0.5 min, then increasing to 80% B within 14.5 min and being maintained at 80% for 3 min with a constant flow rate of 0.4 mL/min.

Dibenzothiophene and its oxidation product dibenzothiophene oxide were identified and quantified by external calibration using authentic standards, based on their retention times, UV absorbtion spectra (230 nm and 260 nm). Dibenzothiophene oxide standard was not commercially available; the quantification of this compound was done using dibenzothiophene sulfone calibration curve.

The peroxygenase oxidised dibenzothiophene yielding a single product, dibenzothiophene oxide (36.2%).

Example 6

Oxidation of Isobutylbenzene

Oxidation of 1 mM isobutylbenzene with 1 mM $H_2O_2$ was carried out with 20% acetonitrile and 5 mM phosphate buffer at pH 6.5, using 0.01 mg/mL of purified peroxygenase (mature peroxygenase encoded by SEQ ID NO: 1) in a total reaction volume of 1 mL. Reaction was performed at room temperature for 5 minutes and sample was then inactivated with 20 µL of 0.5 M $Na_2CO_3$.

Sample was analyzed on an Agilent 1200 HPLC system equipped with a Diode Array Detector (Agilent, Santa Clara Calif., USA) and separated on a Gemini C6-Phenyl (110 Å, 2×150 mm, 3 µm) column from Phenomenex (Torrance Calif., USA) thermostated at 40° C. Two mobile phases were used: (A) 0.1% formic acid, and (B) 0.1% formic acid in acetonitrile.

Separation was run using stepwise gradient starting with 40% B held for 1 min, then increasing to 90% B within 4.5 min and being maintained at 90% for 2 min with a constant flow rate of 0.4 mL/min.

Isobutylbenzene and its possible oxidation products 2-methyl-1-phenyl-1-propanol, isobutyrophenone, 2-methyl-1-phenyl-2-propanol were identified and quantified by external calibration using authentic standards, based on their retention times, UV absorbtion spectra (210 nm).

The peroxygenase oxidised isobutylbenzene yielding a single product, 2-methyl-1-phenyl-1-propanol (2.4%).

Example 7

Oxidation of Benzyl Alcohol

Oxidations of 1 mM benzyl alcohol with 2 mM $H_2O_2$ were carried with 30% acetonitrile and 10 mM acetate (pH 3-5), phosphate (pH 7) or borate buffer (pH 9) at specified pH values, using 0.01 mg/mL of purified peroxygenase (mature peroxygenase encoded by SEQ ID NO: 1) in a total reaction volume of 1 mL. Reactions were performed at room temperature for 25 minutes and stopped by adding 1 µL of catalase (Terminox Ultra 50L, Novozymes).

Samples were analyzed on an Agilent 1200 HPLC system equipped with a Diode Array Detector (Agilent, Santa Clara Calif., USA) and separated on a Zorbax Stable Bond C18 (2) (80 Å, 2.1×50 mm, 1.8 µm) column from Phenomenex (Torrance Calif., USA) thermostated at 40° C. Two mobile phases were used: (A) 0.1% formic acid, and (B) 0.1% formic acid in acetonitrile.

Separations were run using stepwise gradient starting with 5% B held for 4 min, then increasing to 100% B within 6 min with a constant flow rate of 0.5 mL/min.

Benzyl alcohol and its possible oxidation products, benzaldehyde and benzoic acid, were identified and quantified by external calibration using authentic standards, based on their retention times, UV absorbtion spectra (210 nm, 250 nm, and 230 nm respectively).

The peroxygenase oxidised benzyl alcohol yielding a single product, benzaldehyde, as shown in Table 4.

TABLE 4

Comparison of benzaldehyde yields at various pH.

| pH | Benzaldehyde (%) |
|----|------------------|
| 3  | 0.8              |
| 5  | 1.0              |
| 7  | 0                |
| 9  | 0                |

Example 8

Oxidation of 4-hydroxybenzoic Acid

Oxidation of 2 mM 4-hydroxybenzoic acid with 1 mM $H_2O_2$ was carried out in 20% acetonitrile and 10 mM phosphate buffer at pH 6 with 2 mM ascorbic acid, using 0.01 mg/mL of purified peroxygenase (mature peroxygenase encoded by SEQ ID NO: 1) in a total reaction volume of 1 mL. Reactions were performed at room temperature for 15 minutes and stopped by adding 1 µL of catalase (Terminox Ultra 50L, Novozymes).

Sample was analyzed on an Agilent 1200 HPLC system equipped with a Diode Array Detector (Agilent, Santa Clara Calif., USA) and separated on a Zorbax Stable Bond C18 (2) (80 Å, 2.1×50 mm, 1.8 µm) column from Phenomenex (Torrance Calif., USA) thermostated at 40° C. Two mobile phases were used: (A) 0.1% formic acid, and (B) 0.1% formic acid in acetonitrile.

Separation was run using stepwise gradient starting with 5% B held for 4 min, then increasing to 100% B within 6 min with a constant flow rate of 0.5 mL/min.

4-hydroxybenzoic acid and its oxidation product 3,4-dihydroxybenzoic acid was identified and quantified by external calibration using authentic standards, based on their retention times, UV absorbtion spectra at 210 nm.

The peroxygenase oxidised 4-hydroxybenzoic acid yielding a single product, 3,4-dihydroxybenzoic acid (1.0%).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method of producing a polypeptide having peroxygenase activity, comprising:
   (a) cultivating a recombinant host cell which comprises a nucleic acid construct or expression vector comprising a polynucleotide encoding the polypeptide, wherein the polypeptide has at least 80% sequence identity to amino acids 18 to 259 of SEQ ID NO: 2 and the polynucleotide is operably linked to one or more control sequences that direct the production of the polypeptide in the recombinant host cell under conditions conducive for production of the polypeptide; and
   (b) recovering the polypeptide.

2. The method of claim 1, wherein the polypeptide has at least 85% sequence identity to amino acids 18 to 259 of SEQ ID NO: 2.

3. The method of claim 1, wherein the polypeptide has at least 90% sequence identity to amino acids 18 to 259 of SEQ ID NO: 2.

4. The method of claim 1, wherein the polypeptide has at least 95% sequence identity to amino acids 18 to 259 of SEQ ID NO: 2.

5. The method of claim 1, wherein the polypeptide has at least 97% sequence identity to amino acids 18 to 259 of SEQ ID NO: 2.

6. The method of claim 1, wherein the polypeptide comprises amino acids 18 to 259 of SEQ ID NO: 2.

7. The method of claim 1, wherein the polypeptide is encoded by a polynucleotide that hybridizes under high stringency conditions with (i) the mature polypeptide coding sequence of SEQ ID NO: 1, (ii) the cDNA sequence thereof, or (iii) the full-length complement of (i) or (ii).

8. The method of claim 1, wherein the polypeptide is a variant of amino acids 18 to 259 of SEQ ID NO: 2 comprising a substitution, deletion, and/or insertion at one or more positions.

9. The method of claim 1, wherein the polypeptide is a fragment of amino acids 18 to 259 of SEQ ID NO: 2 that has peroxygenase activity.

10. The method of claim 1, wherein the polypeptide comprises an amino acid sequence including the motif:
E-H-D-[G,A]-S-[L,I]-S-R, and
R-[G,A]-P-C-P-X-[M,L]-N-[S,T]-L.

11. A detergent composition, comprising a surfactant and a polypeptide having peroxygenase activity and having at least 80% sequence identity to amino acids 18 to 259 of SEQ ID NO: 2.

12. The detergent composition of claim 11, wherein the polypeptide has at least 85% sequence identity to amino acids 18 to 259 of SEQ ID NO: 2.

13. The detergent composition of claim 11, wherein the polypeptide has at least 90% sequence identity to amino acids 18 to 259 of SEQ ID NO: 2.

14. The detergent composition of claim 11, wherein the polypeptide has at least 95% sequence identity to amino acids 18 to 259 of SEQ ID NO: 2.

15. The detergent composition of claim 11, wherein the polypeptide has at least 97% sequence identity to amino acids 18 to 259 of SEQ ID NO: 2.

16. The detergent composition of claim 11, wherein the polypeptide comprises amino acids 18 to 259 of SEQ ID NO: 2.

17. The detergent composition of claim 11, wherein the polypeptide is a fragment of amino acids 18 to 259 of SEQ ID NO: 2 that has peroxygenase activity.

18. A method for hydroxylation in position 2 or 3 of either end of a substituted or unsubstituted, linear or branched, aliphatic hydrocarbon having at least 3 carbons and having a hydrogen attached to the carbon in position 2 or 3, comprising contacting the aliphatic hydrocarbon with hydrogen peroxide and a polypeptide having peroxygenase activity and having at least 80% sequence identity to amino acids 18 to 259 of SEQ ID NO: 2.

19. The method of claim 18, wherein the polypeptide has at least 85% sequence identity to amino acids 18 to 259 of SEQ ID NO: 2.

20. The method of claim 18, wherein the polypeptide has at least 90% sequence identity to amino acids 18 to 259 of SEQ ID NO: 2.

21. The method of claim 18, wherein the polypeptide has at least 95% sequence identity to amino acids 18 to 259 of SEQ ID NO: 2.

22. The method of claim 18, wherein the polypeptide has at least 97% sequence identity to amino acids 18 to 259 of SEQ ID NO: 2.

23. The method of claim 18, wherein the polypeptide comprises amino acids 18 to 259 of SEQ ID NO: 2.

24. The method of claim 18, wherein the polypeptide is a fragment of amino acids 18 to 259 of SEQ ID NO: 2 that has peroxygenase activity.

* * * * *

SEQUENCE LISTING

```
<160> NUMBER OF SEQ ID NOS: 18

<210> SEQ ID NO 1
<211> LENGTH: 928
<212> TYPE: DNA
<213> ORGANISM: Aspergillus carbonarius
<220> FEATURE:
<221> NAME/KEY: CDS
<222> LOCATION: (1)..(100)
<220> FEATURE:
<221> NAME/KEY: sig_peptide
<222> LOCATION: (1)..(51)
<220> FEATURE:
<221> NAME/KEY: Intron
<222> LOCATION: (101)..(144)
<220> FEATURE:
<221> NAME/KEY: CDS
<222> LOCATION: (145)..(385)
<220> FEATURE:
<221> NAME/KEY: Intron
<222> LOCATION: (386)..(443)
<220> FEATURE:
<221> NAME/KEY: CDS
<222> LOCATION: (444)..(712)
<220> FEATURE:
<221> NAME/KEY: Intron
<222> LOCATION: (713)..(758)
<220> FEATURE:
<221> NAME/KEY: CDS
<222> LOCATION: (759)..(925)

<400> SEQUENCE: 1 atg aag tcc act att ctt ctt att acc acc tct ttg agc cag gcc ctg      48
Met Lys Ser Thr Ile Leu Leu Ile Thr Thr Ser Leu Ser Gln Ala Leu
1               5                   10                  15 gcc cag gtt tca tcc cac cca ttt ccc tgg tcg gct ccc ggg ccc aac      96
Ala Gln Val Ser Ser His Pro Phe Pro Trp Ser Ala Pro Gly Pro Asn
                20                  25                  30 gat g gtgagtcagg ttgtcgctgg aataacaaaa actgaagggt acag tg  cga       149
Asp                                                    Val Arg
                                                        35
```

```
ggg cct tgt ccc atg ctg aac aca ctt gcg aac cac gga ttc cta ccc      197
Gly Pro Cys Pro Met Leu Asn Thr Leu Ala Asn His Gly Phe Leu Pro
             40                  45                  50 cac gat ggc aag gat att aca gaa gac cgc atc gtg atg gta cta aac      245
His Asp Gly Lys Asp Ile Thr Glu Asp Arg Ile Val Met Val Leu Asn
 55                  60                  65 aat tct ctc aac ttg gat gaa gaa ctt tcc cag ttt ctg ttc aag gag      293
Asn Ser Leu Asn Leu Asp Glu Glu Leu Ser Gln Phe Leu Phe Lys Glu
         70                  75                  80 gca ctg acc aca aac ccg gat ccc aac gct act act ttc tct ctg aat      341
Ala Leu Thr Thr Asn Pro Asp Pro Asn Ala Thr Thr Phe Ser Leu Asn
     85                  90                  95 gat ctc agt cgt cat aat att ctg gag cat gat gcc agt ttg ag           385
Asp Leu Ser Arg His Asn Ile Leu Glu His Asp Ala Ser Leu Ser
100                 105                 110 gtgtgttcat tcactatctc tacaccttgc aaaccatgat tcatcctgac caatgcag c    444 cgc cag gat tac tat ttc gga gat aac cac gac ttc aac cag acc gtc      492
Arg Gln Asp Tyr Tyr Phe Gly Asp Asn His Asp Phe Asn Gln Thr Val
115                 120                 125                 130 ttc aac gaa aca cga tca tat tgg acc gcc cct ctc atc gac ttc aat      540
Phe Asn Glu Thr Arg Ser Tyr Trp Thr Ala Pro Leu Ile Asp Phe Asn
             135                 140                 145 gca gcc gca caa gcc cgc ctg gct cgt gtg aat acc tcg atg gcc acc      588
Ala Ala Ala Gln Ala Arg Leu Ala Arg Val Asn Thr Ser Met Ala Thr
         150                 155                 160 aat ccc act tat acc gag tcg gaa act ggc ctg gcg ttc agc tat ggg      636
Asn Pro Thr Tyr Thr Glu Ser Glu Thr Gly Leu Ala Phe Ser Tyr Gly
     165                 170                 175 gag agt gct gcc tac atg atc gta ttt gcc gag ggt tcc gag acg gct      684
Glu Ser Ala Ala Tyr Met Ile Val Phe Ala Glu Gly Ser Glu Thr Ala
180                 185                 190 aat cga tca tgg gtg gaa tac ttc ttt g gtaagccatt ccttgtctaa          732
Asn Arg Ser Trp Val Glu Tyr Phe Phe
195                 200 cctagggagt tattaatgtt gtatag ag  cat gag cgt ctg ccc cag cag ctt     784
                                 Glu His Glu Arg Leu Pro Gln Gln Leu
                                             205                 210 ggt tgg aca aaa cct caa gag agt atc tcg tca tcg gtc ctt ata gac      832
Gly Trp Thr Lys Pro Gln Glu Ser Ile Ser Ser Ser Val Leu Ile Asp
             215                 220                 225 aca gtc aca ggc att gca aac gct tct aat gct tct tct ctg gtg gtt      880
Thr Val Thr Gly Ile Ala Asn Ala Ser Asn Ala Ser Ser Leu Val Val
 230                 235                 240 gcc gag ctg ctt gat ttt gtt gct ttg cac atg ggt cgc ttg cca tga      928
Ala Glu Leu Leu Asp Phe Val Ala Leu His Met Gly Arg Leu Pro
245                 250                 255

<210> SEQ ID NO 2
<211> LENGTH: 259
<212> TYPE: PRT
<213> ORGANISM: Aspergillus carbonarius

<400> SEQUENCE: 2

Met Lys Ser Thr Ile Leu Leu Ile Thr Thr Ser Leu Ser Gln Ala Leu
  1               5                  10                  15

Ala Gln Val Ser Ser His Pro Phe Pro Trp Ser Ala Pro Gly Pro Asn
             20                  25                  30

Asp Val Arg Gly Pro Cys Pro Met Leu Asn Thr Leu Ala Asn His Gly
         35                  40                  45
```

```
Phe Leu Pro His Asp Gly Lys Asp Ile Thr Glu Asp Arg Ile Val Met
        50                  55                  60

Val Leu Asn Asn Ser Leu Asn Leu Asp Glu Glu Leu Ser Gln Phe Leu
 65                  70                  75                  80

Phe Lys Glu Ala Leu Thr Thr Asn Pro Asp Pro Asn Ala Thr Thr Phe
                85                  90                  95

Ser Leu Asn Asp Leu Ser Arg His Asn Ile Leu Glu His Asp Ala Ser
            100                 105                 110

Leu Ser Arg Gln Asp Tyr Tyr Phe Gly Asp Asn His Asp Phe Asn Gln
            115                 120                 125

Thr Val Phe Asn Glu Thr Arg Ser Tyr Trp Thr Ala Pro Leu Ile Asp
        130                 135                 140

Phe Asn Ala Ala Gln Ala Arg Leu Ala Arg Val Asn Thr Ser Met
145                 150                 155                 160

Ala Thr Asn Pro Thr Tyr Thr Glu Ser Glu Thr Gly Leu Ala Phe Ser
                165                 170                 175

Tyr Gly Glu Ser Ala Ala Tyr Met Ile Val Phe Ala Glu Gly Ser Glu
            180                 185                 190

Thr Ala Asn Arg Ser Trp Val Glu Tyr Phe Phe Glu His Glu Arg Leu
        195                 200                 205

Pro Gln Gln Leu Gly Trp Thr Lys Pro Gln Glu Ser Ile Ser Ser Ser
    210                 215                 220

Val Leu Ile Asp Thr Val Thr Gly Ile Ala Asn Ala Ser Asn Ala Ser
225                 230                 235                 240

Ser Leu Val Val Ala Glu Leu Leu Asp Phe Val Ala Leu His Met Gly
                245                 250                 255

Arg Leu Pro

<210> SEQ ID NO 3
<211> LENGTH: 8
<212> TYPE: PRT
<213> ORGANISM: Artificial
<220> FEATURE:
<223> OTHER INFORMATION: Motif sequence

<400> SEQUENCE: 3

Glu His Asp Gly Ser Leu Ser Arg
1               5

<210> SEQ ID NO 4
<211> LENGTH: 8
<212> TYPE: PRT
<213> ORGANISM: Artificial
<220> FEATURE:
<223> OTHER INFORMATION: Motif sequence

<400> SEQUENCE: 4

Glu His Asp Ala Ser Leu Ser Arg
1               5

<210> SEQ ID NO 5
<211> LENGTH: 8
<212> TYPE: PRT
<213> ORGANISM: Artificial
<220> FEATURE:
<223> OTHER INFORMATION: Motif sequence

<400> SEQUENCE: 5

Glu His Asp Gly Ser Ile Ser Arg
1               5
```

-continued

```
<210> SEQ ID NO 6
<211> LENGTH: 8
<212> TYPE: PRT
<213> ORGANISM: Artificial
<220> FEATURE:
<223> OTHER INFORMATION: Motif sequence

<400> SEQUENCE: 6

Glu His Asp Ala Ser Ile Ser Arg
1               5

<210> SEQ ID NO 7
<211> LENGTH: 8
<212> TYPE: PRT
<213> ORGANISM: Artificial
<220> FEATURE:
<223> OTHER INFORMATION: Motif sequence
<220> FEATURE:
<221> NAME/KEY: MISC_FEATURE
<222> LOCATION: (4)..(4)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is Leu or Ile

<400> SEQUENCE: 7

Glu His Asp Xaa Ser Xaa Ser Arg
1               5

<210> SEQ ID NO 8
<211> LENGTH: 52
<212> TYPE: DNA
<213> ORGANISM: Artificial
<220> FEATURE:
<223> OTHER INFORMATION: Cloning primer forward

<400> SEQUENCE: 8
acacaactgg ggatccacca tgaagtccac tattcttctt attaccacct ct            52

<210> SEQ ID NO 9
<211> LENGTH: 47
<212> TYPE: DNA
<213> ORGANISM: Artificial
<220> FEATURE:
<223> OTHER INFORMATION: Cloning primer reverse

<400> SEQUENCE: 9
agatctcgag aagcttatct ttggtactaa tggtccaggc aaatagt                  47

<210> SEQ ID NO 10
<211> LENGTH: 10
<212> TYPE: PRT
<213> ORGANISM: Artificial
<220> FEATURE:
<223> OTHER INFORMATION: Motif sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 10

Arg Gly Pro Cys Pro Xaa Met Asn Ser Leu
1               5                   10

<210> SEQ ID NO 11
<211> LENGTH: 10
<212> TYPE: PRT
<213> ORGANISM: Artificial
```

```
<220> FEATURE:
<223> OTHER INFORMATION: Motif sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 11

Arg Ala Pro Cys Pro Xaa Met Asn Ser Leu
1               5                   10

<210> SEQ ID NO 12
<211> LENGTH: 10
<212> TYPE: PRT
<213> ORGANISM: Artificial
<220> FEATURE:
<223> OTHER INFORMATION: Motif sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 12

Arg Gly Pro Cys Pro Xaa Leu Asn Ser Leu
1               5                   10

<210> SEQ ID NO 13
<211> LENGTH: 10
<212> TYPE: PRT
<213> ORGANISM: Artificial
<220> FEATURE:
<223> OTHER INFORMATION: Motif sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 13

Arg Ala Pro Cys Pro Xaa Leu Asn Ser Leu
1               5                   10

<210> SEQ ID NO 14
<211> LENGTH: 10
<212> TYPE: PRT
<213> ORGANISM: Artificial
<220> FEATURE:
<223> OTHER INFORMATION: Motif sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 14

Arg Gly Pro Cys Pro Xaa Met Asn Thr Leu
1               5                   10

<210> SEQ ID NO 15
<211> LENGTH: 10
<212> TYPE: PRT
<213> ORGANISM: Artificial
<220> FEATURE:
<223> OTHER INFORMATION: Motif sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 15

Arg Ala Pro Cys Pro Xaa Met Asn Thr Leu
1               5                   10
```

```
<210> SEQ ID NO 16
<211> LENGTH: 10
<212> TYPE: PRT
<213> ORGANISM: Artificial
<220> FEATURE:
<223> OTHER INFORMATION: Motif sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 16

Arg Gly Pro Cys Pro Xaa Leu Asn Thr Leu
 1               5                  10

<210> SEQ ID NO 17
<211> LENGTH: 10
<212> TYPE: PRT
<213> ORGANISM: Artificial
<220> FEATURE:
<223> OTHER INFORMATION: Motif sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 17

Arg Ala Pro Cys Pro Xaa Leu Asn Thr Leu
 1               5                  10

<210> SEQ ID NO 18
<211> LENGTH: 10
<212> TYPE: PRT
<213> ORGANISM: Artificial
<220> FEATURE:
<223> OTHER INFORMATION: Motif sequence
<220> FEATURE:
<221> NAME/KEY: MISC_FEATURE
<222> LOCATION: (2)..(2)
<223> OTHER INFORMATION: Xaa is Gly or Ala
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Leu or Met
<220> FEATURE:
<221> NAME/KEY: MISC_FEATURE
<222> LOCATION: (9)..(9)
<223> OTHER INFORMATION: Xaa is Ser or Thr

<400> SEQUENCE: 18

Arg Xaa Pro Cys Pro Xaa Xaa Asn Xaa Leu
 1               5                  10
```